United States Patent
Sharifi-Mehr et al.

(10) Patent No.: US 11,426,258 B2
(45) Date of Patent: Aug. 30, 2022

(54) TAP MARKER WITH FLEXIBLE EXTENSION AND ASSOCIATED INSTRUMENTS

(71) Applicant: Stryker European Operations Limited, Carrigtwohill (IE)

(72) Inventors: Amir Ali Sharifi-Mehr, Bloomingdale, NJ (US); Shawn D. Stad, Lakeville, MA (US)

(73) Assignee: Stryker European Operations Limited

( * ) Notice: Subject to any disclaimer, the term of this patent is extended or adjusted under 35 U.S.C. 154(b) by 434 days.

(21) Appl. No.: 16/717,452

(22) Filed: Dec. 17, 2019

(65) Prior Publication Data
US 2020/0197124 A1    Jun. 25, 2020

Related U.S. Application Data

(60) Provisional application No. 62/783,349, filed on Dec. 21, 2018.

(51) Int. Cl.
*A61B 17/70* (2006.01)
*A61B 90/00* (2016.01)

(52) U.S. Cl.
CPC ...... *A61B 90/39* (2016.02); *A61B 2090/3916* (2016.02); *A61B 2090/3937* (2016.02); *A61B 2090/3945* (2016.02); *A61B 2090/3983* (2016.02); *A61B 2090/3991* (2016.02)

(58) Field of Classification Search
CPC ............ A61B 90/39; A61B 2090/3916; A61B 2090/3937; A61B 2090/3945; A61B 2090/3983; A61B 2090/3991
See application file for complete search history.

(56) References Cited

U.S. PATENT DOCUMENTS

| | | | |
|---|---|---|---|
| 5,928,139 A | 7/1999 | Koros et al. | |
| 6,090,113 A | 7/2000 | Le Couedic et al. | |
| 6,648,891 B2 | 11/2003 | Kim | |
| 6,858,030 B2 | 2/2005 | Martin et al. | |
| 7,156,874 B2 | 1/2007 | Paponneau et al. | |
| 7,468,064 B2 * | 12/2008 | Bruneau | A61B 17/8605 606/99 |
| 7,637,950 B2 | 12/2009 | Baccelli et al. | |

(Continued)

FOREIGN PATENT DOCUMENTS

DE    10352027 A1    6/2005
WO    9915097 A2    4/1999

OTHER PUBLICATIONS

Extended European Search Report for EP19216399.6 dated Jun. 17, 2020; 3 pages.

*Primary Examiner* — Kevin T Truong
*Assistant Examiner* — Tracy L Kamikawa
(74) *Attorney, Agent, or Firm* — Lerner, David, Littenberg, Krumholz & Mentlik, LLP (57) ABSTRACT

A spinal marking system includes a marker having a threaded member and a flexible member connected to the threaded member. The flexible member has a length longer than that of the threaded member. The system also includes a navigation tool having a shaft configured to connect to the threaded member. The navigation tool also includes a navigation array connected to the shaft. The navigation array having a plurality of fiducials that are configured to communicate with a robotic system.

16 Claims, 8 Drawing Sheets

(56) References Cited

U.S. PATENT DOCUMENTS

| | | | |
|---|---|---|---|
| 7,763,030 B2* | 7/2010 | Blau | A61B 17/7083 606/99 |
| 7,985,256 B2 | 7/2011 | Grotz et al. | |
| 8,157,809 B2 | 4/2012 | Butters et al. | |
| 8,216,317 B2 | 7/2012 | Thibodeau | |
| 8,333,770 B2* | 12/2012 | Hua | H04N 21/482 606/279 |
| 2003/0055430 A1 | 3/2003 | Kim | |
| 2004/0147928 A1* | 7/2004 | Landry | A61B 90/92 606/264 |
| 2005/0021040 A1 | 1/2005 | Bertagnoli | |
| 2005/0203533 A1 | 9/2005 | Ferguson et al. | |
| 2006/0079903 A1* | 4/2006 | Wong | A61B 17/8891 606/328 |
| 2006/0235422 A1 | 10/2006 | Keller | |
| 2006/0241769 A1 | 10/2006 | Gordon et al. | |
| 2010/0057136 A1 | 3/2010 | Heiges et al. | |
| 2010/0331849 A1 | 12/2010 | Riesinger et al. | |
| 2013/0310942 A1 | 11/2013 | Abdou | |
| 2014/0012269 A1 | 1/2014 | Bass | |
| 2015/0066042 A1 | 3/2015 | Cummins et al. | |
| 2016/0106408 A1 | 4/2016 | Ponmudi et al. | |
| 2016/0354153 A1* | 12/2016 | Hodgson | A61B 90/39 |
| 2017/0196597 A1 | 7/2017 | Corbin et al. | |
| 2017/0360515 A1 | 12/2017 | Kozak et al. | |
| 2018/0092699 A1 | 4/2018 | Finley | |
| 2018/0146987 A1 | 5/2018 | Corbin et al. | |
| 2018/0153585 A1 | 6/2018 | Levine | |
| 2018/0325608 A1 | 11/2018 | Kang et al. | |
| 2019/0269469 A1* | 9/2019 | Bush, Jr. | A61B 34/76 |

* cited by examiner

TAP MARKER WITH FLEXIBLE EXTENSION AND ASSOCIATED INSTRUMENTS

CROSS-REFERENCE TO RELATED APPLICATION

The present application claims the benefit of the filing date of U.S. Provisional Patent Application No. 62/783,349 filed Dec. 21, 2018, the disclosure of which is hereby incorporated herein by reference.

BACKGROUND OF THE INVENTION

Spinal stabilization typically involves the insertion of bone screws into adjacent vertebrae and the connection of such vertebrae via rods connected to the screws. Bone holes for such bone screws are often formed early in the procedure as such holes may be used for various steps of the procedure, such as distraction and compression of adjacent vertebrae. In this regard, temporary threaded devices may be inserted into the bone so that such threaded devices can be used by other instruments, such as distractors, to perform the various steps of the procedure. One advantage of using temporary threaded devices, such as during decompression, is that they can provide a landmark to track the locations of bony features during the procedure.

However, tracking difficulties still remain. For example, in minimally invasive surgeries (MIS), equipment attached to the bone, such as a temporary bone screw, may be easily obscured by soft tissue. Time can be lost trying to relocate the bone and equipment attached thereto which may unnecessarily extend the length of the procedure. On the other hand, devices, such as k-wires, that extend from the MIS incision so as to be readily visible by the operator may require the operator to work around such devices and may, therefore, limit the operating space within which the operator has to work. Additionally, in robotic procedures, the bone may be moved out of registration with the robot's coordinate system such that inaccuracies in final screw placement can result. Thus, further improvements are desirable.

BRIEF SUMMARY OF THE INVENTION

The present disclosure describes devices, systems, and methods that can, among other things, help an operator track anatomical features during a surgical procedure. In particular, a tap marker assembly is described as having a tap marker and insertion/removal body. The tap marker includes a tap for cutting threads into a bone for a permanent bone screw and a flexible member extending from the tap. The flexible member can extend from an incision, such as an MIS incision, to help an operator keep track of the patient's anatomy throughout the procedure. The flexible member can be easily moved out of the way by the operator due to its flexibility so as to not interfere with the procedure. The insertion of the tap marker into bone may be aided by the insertion/removal body which may act as an adapter that allows tap marker to be insertion/removal device via a driver that may also be used to drive permanent bone screws into the bone, which can help reduce the total number of instruments needed to perform the procedure.

Also described is a navigation assembly which includes the tap marker and a navigation tool. The navigation tool may have a cannulated shaft which can receive the flexible member and connect to the head of the tap. The navigation tool may also include a navigation array that comprises an array of fiducials that may be used by a robotic system for registration of the bone so that a preoperative plan can be carried out by the robot.

In one aspect of the present disclosure, a spinal marking system includes a marker having a threaded member and a flexible member connected to the threaded member. The flexible member has a length longer than that of the threaded member. The system also includes a navigation tool that has a shaft configured to connect to the threaded member. The navigation tool also has a navigation array connected to the shaft. The navigation array has a plurality of fiducials that are configured to communicate with a robotic system.

Additionally, the plurality of fiducials may actively emit light or passively reflect light. The threaded member may have a threaded shaft with at least one flute and a head extending from the threaded shaft. The flexible member may be connected to and extend from the head. The marker may further include a post received within an opening in the head and extending therefrom. The post may have an opening extending entirely therethrough. The flexible member may extend through the opening of the post. The marker may further include a crimp ring crimped about an end of the flexible member and disposed within the opening in the head of the threaded member. The head of the threaded member may include a tool engagement portion comprised of a plurality of intersecting planar faces. The shaft of the navigation tool may have a plurality of intersecting planar faces configured to interface with those of the tool engagement portion to prevent relative rotation between the navigation tool and the marker when the navigation tool is connected to the threaded member.

Continuing with this aspect, the system may further include an insertion body removably connectable to the marker. The insertion body may have a head and a shaft extending from the head. The head may have a threaded inner surface. The threaded member may have a male engagement portion, and the shaft of the insertion body may have a female engagement portion configured to receive the male engagement portion of the threaded member. The male and female engagement portions may each have corresponding intersecting planar faces and when said planar faces of the threaded member and insertion body interface, relative rotation between the threaded member and insertion body is prevented. The system may also include a retaining ring, and the marker may include a post extending from the threaded member. The retaining ring may be configured to engage the post and insertion body to limit relative axial movement between the post and the insertion body. The insertion body may define an opening extending therethrough such that when the male and female engagement portions engage, the flexible member extends from one end of the insertion body and the threaded member extends from another end of the insertion body. The system may also include a driver having a threaded exterior surface configured to threadedly engage the threaded inner surface of insertion body.

In another aspect of the present disclosure, a tap marker assembly includes a tap marker that includes a tap that has a threaded shaft and a head that extends from the threaded shaft. The tap marker also has a flexible member connected to and extending from the head of the tap. The flexible member has a length greater than that of the tap. The assembly also includes an insertion body removably connected to the tap and has an opening extending through the insertion body such that the flexible member extends from one end of the insertion body and the tap extends from another end of the insertion body when the insertion body is connected to the tap.

Additionally, the tap may include a male engagement portion, and the opening of the insertion body may include a female engagement portion configured to mate with the male engagement portion of the tap. The male and female engagement portions may each include corresponding planar faces that interface with each other to prevent relative rotation between the tap and connection portion. The male and female engagement portions may each comprise corresponding threaded surfaces for threaded connection of the same. The insertion body may include a head and a shaft extending from the head. The head may have a larger cross-sectional dimension than the shaft and may have a threaded inner surface for engagement with threads of a driver. The tap marker may further include a post connected to the head of the tap and extending therefrom. The post may have a longitudinal opening through which the flexible member extends and a circumferential groove extending about an axis defined by the longitudinal opening. The insertion body may be connected to the post via a retention ring positioned between the insertion body and post and at least partially within the circumferential groove. The assembly may also include a crimp ring crimped to an end of the flexible member and positioned within the head of tap such that it is positioned between threaded shaft and post. The post may be connected to the head of the tap via one of a threaded connection or a press-fit connection. The flexible material may be nitinol.

In a further aspect of the present disclosure, a method of marking a bone includes connecting a driver to a threaded member such that a flexible member connected to and extending from the threaded member is positioned within an opening within the driver. The flexible member has a length longer than that of the threaded member. The method also includes inserting the threaded member through an incision, driving the threaded member into a bone, and disconnecting the inserter from the threaded member such that the flexible member extends from the threaded member and through the incision.

Additionally, connecting the driver to the threaded member may include connecting the driver to an adapter connected to a head of the threaded member, and disconnecting the driver from the threaded member may include removing the adapter from the threaded member while the adapter remains connected to the driver. Connecting the driver to the adapter may include threading threads of the driver with threads of the adapter. The threads of the adapter may be located on an inner surface of a head thereof. Also, disconnecting the driver from the threaded member may include pulling the driver and adapter axially along a longitudinal axis of the threaded member. The method may also include positioning a navigation tool over the flexible member and onto the threaded member. The navigation tool may have a navigation array comprised of a plurality of fiducials that are configured to one of actively emit light or passively reflect light. The method may also include registering the bone with a robotic system by detecting light emitted or reflected by the fiducials. The bone may be a pedicle of a vertebra.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain devices, it should be understood that such directions are described with regard to the device's orientation and position relative to an operator during exemplary application to the human body. Thus, as used herein, the term "proximal" means closer to the operator or in a direction toward the operator, and the term "distal" means more distant from the operator or in a direction away from the operator. Also, as used herein, the terms "about," "generally," and "substantially" are intended to mean that slight deviations from absolute are included within the scope of the term so modified. To aid the Patent Office and any readers of any patent issued on this application in interpreting the claims appended hereto, Applicant notes that it does not intend any of the appended claims or claim elements to invoke 35 U.S.C. § 112(f) unless the words "means for" or "step for" are explicitly used in the particular claim.

FIGS. 1A-1F depict a tap marker assembly 100 according to an embodiment of the present disclosure. Tap marker assembly 100 generally includes a tap marker 100', an insertion/removal body 150, and a retention ring 160.

Figure 1A:
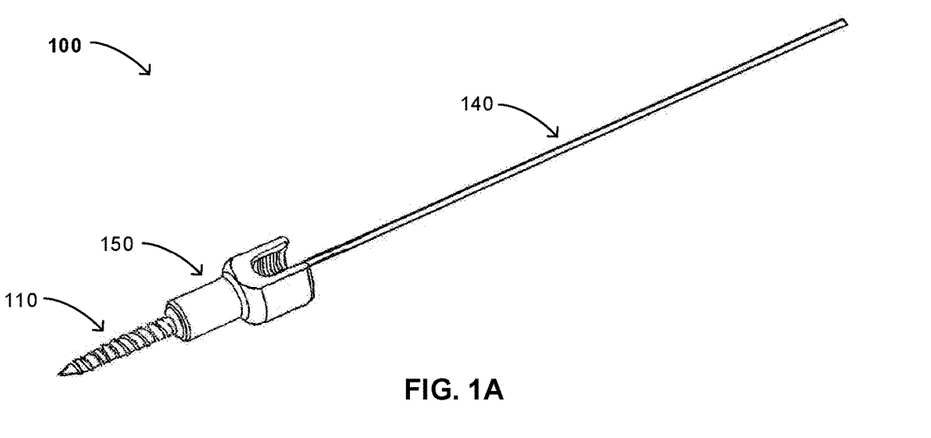
FIG. 1A is a perspective view of a tap marker assembly according to an embodiment of the disclosure.
Figure 1B:
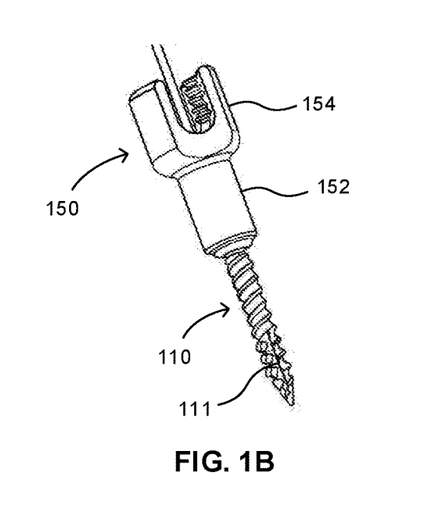
FIG. 1B is an enhanced view of a portion of the tap marker assembly of FIG. 1A.
Figure 1C:
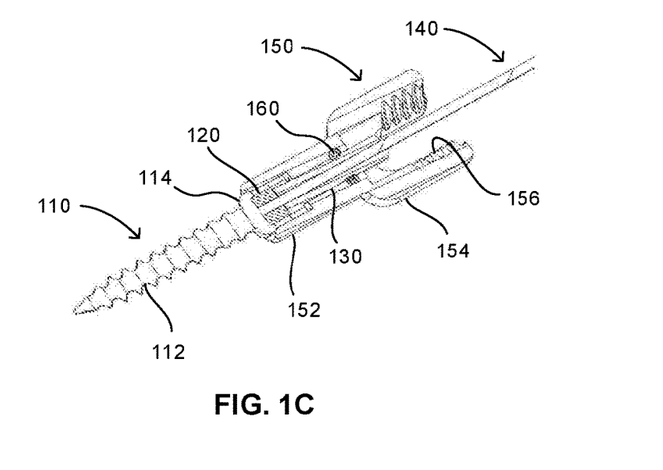
FIG. 1C is a cross-sectional view of the tap marker assembly of FIG. 1B taken along a midline thereof.
Figure 1D:
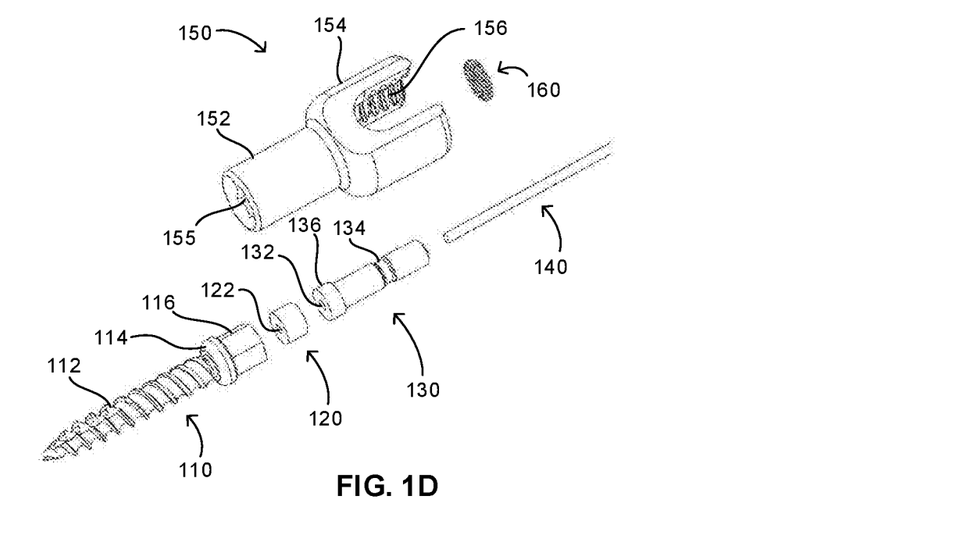
FIGS. 1D and 1E are exploded views of the tap marker assembly of FIG. 1A.
Figure 1E:
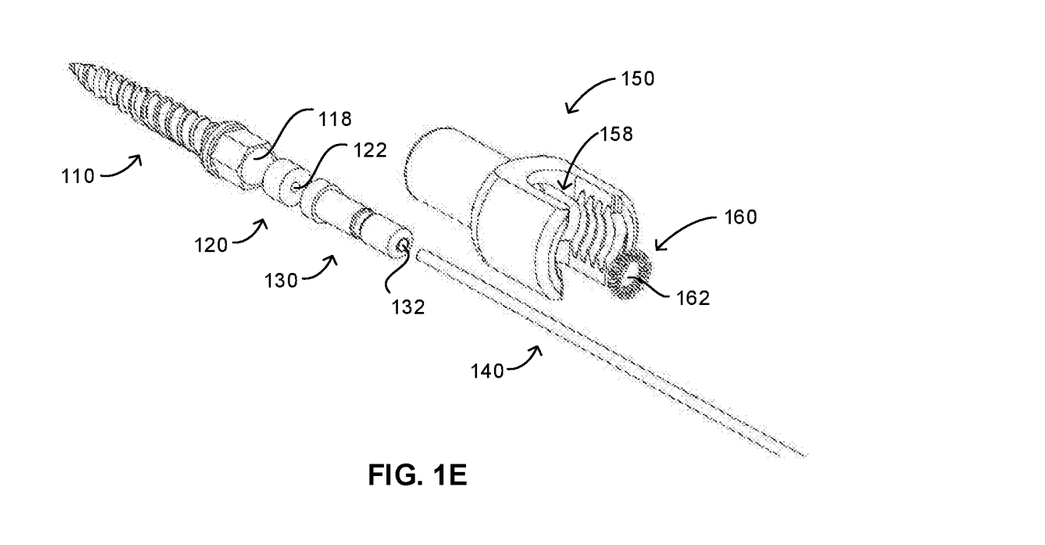
Figure 1F:
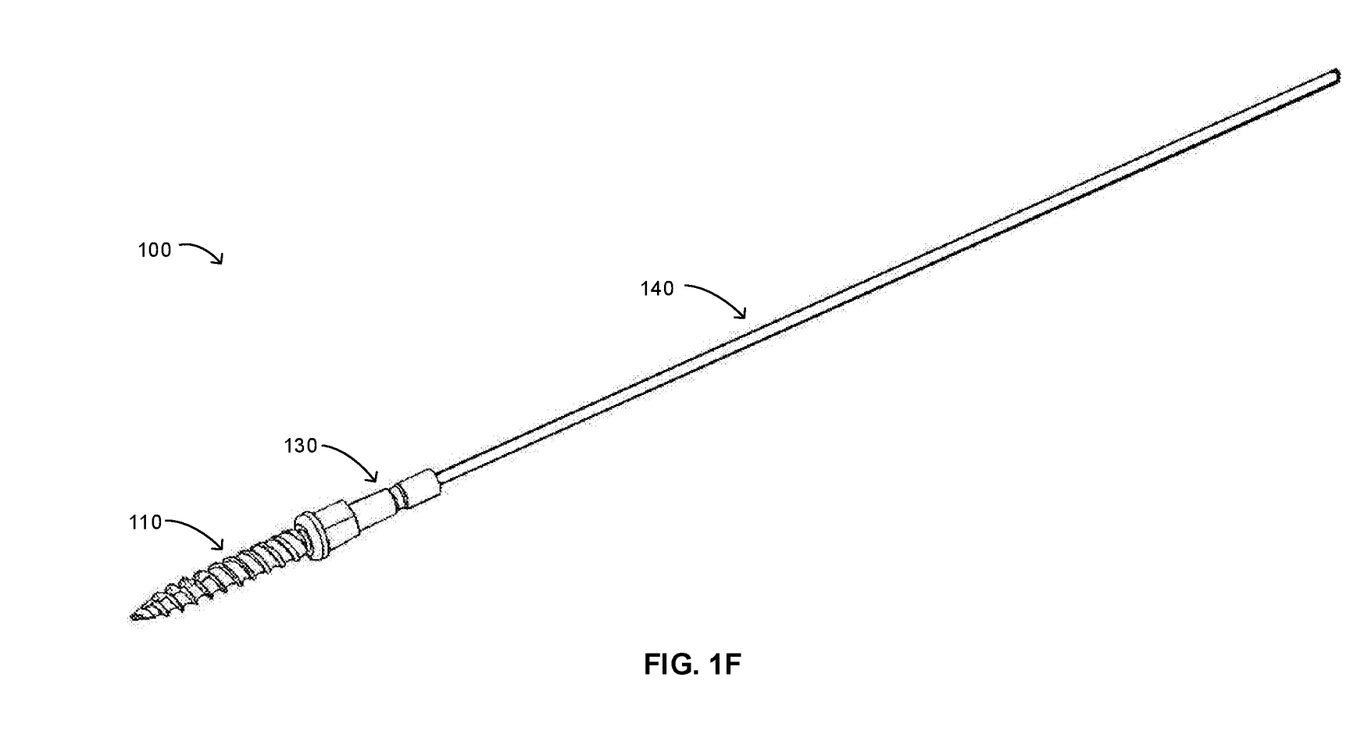
FIG. 1F is a perspective view of a tap marker of the tap marker assembly of FIG. 1A.

Tap marker 100' includes a tap or threaded fastener/member 110, crimp ring 120, marker post 130, and flexible member 140, as best shown in FIGS. 1C-1E. Tap 110 includes a threaded shaft 112 and a head 114. Threaded shaft 112 includes a cutting flute 111 and thread helically extending along at least a portion of the shaft's length. Cutting flute 111 allows tap 110 to self-drill into bone. Of course, tap 110 could also be formed without a flute and inserted into a pre-drilled hole. Head 114 extends proximally from threaded shaft 112 and includes a tool engaging portion or male engagement portion 116 which, in the embodiment depicted, includes a plurality of planar faces, such as in a hexagonal configuration. In addition, an opening 118 extends distally into the head 114 from a proximal end thereof, as best shown in FIG. 1E. Such opening 118 is configured to receive crimp ring 120 and at least a portion of marker post 130, as describe below.

Flexible member 140 is an elongate rod that is made of a flexible material such a shape-memory or super elastic material, such as nitinol, for example. Crimp ring 120 has an opening 122 that is configured to receive flexible member and an outer diameter sized to be received in opening 118 of tap 110. Marker post 130 has a length greater than that of crimp ring 120 and also has an opening 132 that extends through its length. Marker post 130 also has a ring retention groove or circumferential groove 134 extending about a longitudinal axis thereof and an enlarged end 136 that is configured to be received within opening of tap 110.

Insertion/removal body 150 includes a tulip head 154 and cylindrical shaft 152 extending distally therefrom. Tulip head 154 is similarly configured to a tulip of a pedicle screw. An example of such at pedicle screw tulip can be found in U.S. Publication No. 2018/0146987, which is incorporated by reference herein in its entirety. Thus, tulip 154 has a transverse channel 158 that extends in a direction transverse to a longitudinal axis of tulip head 154. However, in some embodiments, tulip head 154 may not include transverse channel 158. In addition, tulip head 154 includes an opening that extends longitudinally through tulip head 154 and is at least partially defined by a threaded inner surface 156 of head 154. Such threaded inner surface 156 is configured to engage an insertion and removal instrument, as discussed in more detail below. Cylindrical shaft 152 also includes an opening that extends therethrough and communicates with the longitudinal opening of tulip head 154 such that a longitudinal opening 155 extends through the entirety of insertion/removal body 150. At least at the distal end of shaft 152, opening 155 is defined by a female engagement portion with intersecting planar inner surfaces configured to correspondingly engage tool engagement portion 116 of tap head 114.

Retention ring 160 is shown as a coiled spring that is formed into an annular ring. Such retention ring 160 is received in a groove (not shown) within inner surface 156 of tulip head 154 and has an opening 162 that is coaxial with opening 155 when disposed within body 150. Retention ring 160 could also be a rubber O-ring or the like.

As assembled, crimp ring 120 is disposed within opening 118 of tap head 110. Tap marker post 130 is partially received within opening 118 and is secured to tap head 110, such as via a press-fit, weld, or the like. The securement of tap marker post 130 to tap head 110 also secures crimp ring 120 to tap head 110 as crimp ring 120 is trapped within opening 118 via tap marker post 130. Marker post 130 extends from a proximal end of tap 110 a length sufficient to allow a distraction device to engage post 130 for distraction and compression. An exemplary distractor device which can engage either tool engagement portion 116 or post 130 of tap marker 100' can be found in U.S. Publication No. 2017/0196597, which is hereby incorporated by reference herein in its entirety. Flexible member 140 extends entirely through marker post 130 and into crimp ring 120. Crimp ring 120 is crimped onto a distal end of flexible member 140 so as to secure flexible member 140 to tap 110.

Insertion/removal body 150 removeably connects to tap marker such that body 150 can be removed in-situ in order to reduce the profile of assembly 100. In this regard, when insertion/removal body 150 is connected to tap marker 110, cylindrical shaft 152 is positioned over tap marker 100' such that tool engaging portion 116 is received within opening 155 of insertion/removal body 150. The faceted surfaces of tool engaging portion 116 and cylindrical shaft 152 prevent rotational movement of insertion/removal body 150 relative to tap 110 and consequently also allows a torque applied to insertion/removal body 150 to be transmitted to tap marker 100'. Post 130 is positioned within insertion/removal body 150, and retaining ring 160 is positioned within groove 134 between post 130 and insertion/removal body 150 so that retaining ring 160 creates a positive connection between post 130 and insertion/removal body 150 in order to prevent incidental axial movement of insertion/removal body 150 relative to tap marker 100' without deliberate manipulation by an operator. However, it should be understood that body 150 can be connected to post 130 via mechanisms other than retaining ring 160 in order to axially secure body 150 thereto until it is desired to remove body 150 therefrom. Examples of such mechanisms include a ball plunger, flexible finger, and quick-connect mechanism, such as a ball-bearing type quick-connect and the like. Flexible member 140 extends proximally from insertion/removal body 150 once body 150 is connected to post 130.

Figure 2A:
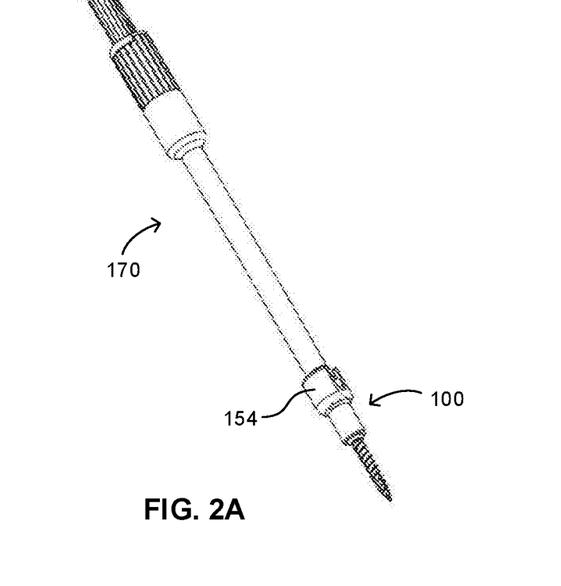
FIGS. 2A-2G illustrate a method of using the tap marker assembly of FIG. 1A.
Figure 2B:
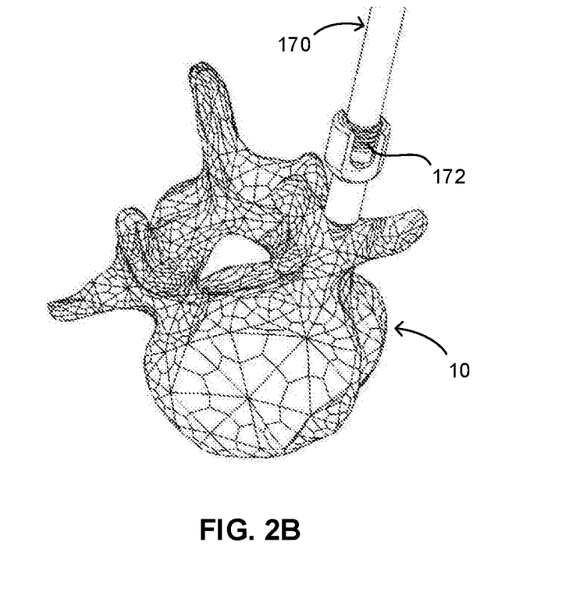

Tap marker assembly 100 can be included in a kit or system with other devices. One such device may be a tap marker insertion/removal device or driver 170. Such insertion/removal device 170 is depicted in FIGS. 2A and 2B. Insertion/removal device 170 is cannulated so that it can receive flexible member 140 and may be manually manipulated by a surgeon or robotically held and controlled by an end effector of a robotic system. Insertion/removal device 170 also includes a distal end that has external threads 172 configured to threadedly engage inner threads of tulip head 154, as best shown in FIG. 2B. In this regard, insertion/removal device 170 can also engage and insert pedicle screws. As such, both tap marker assembly 100 and pedicle screws can be driven into a vertebra via the same insertion/removal device 170 which helps reduce the total number of instruments needed in the operating theater. However, it is contemplated that a separate insertion/removal device can be used. For example, an insertion/removal device may be cannulated and have a female hex end that is configure to engage tool engaging portion 116 of tap marker 110 so that such insertion/removal device can drive tap marker 100' into bone without insertion/removal body 150 being connected to tap marker 100'. Thus, insertion/removal body 150 is in effect an adapter that allows tap marker 100' to be connected to insertion/removal devices, such as device 170, that may already be available to the operator for other devices used in the procedure so as to reduce the total number of instruments needed.

Figure 2C:
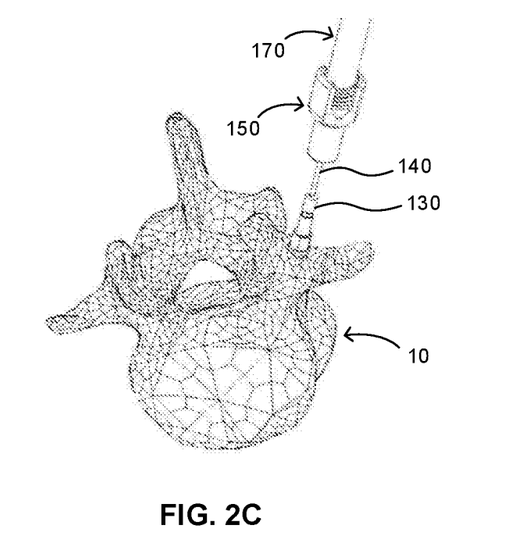
Figure 2D:
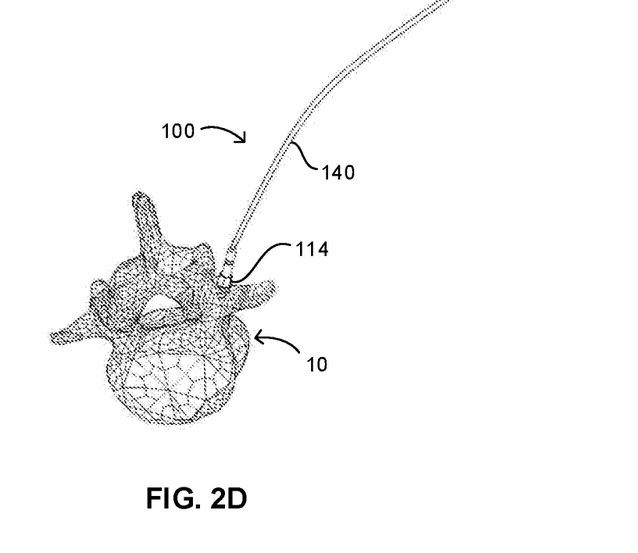
Figure 2E:
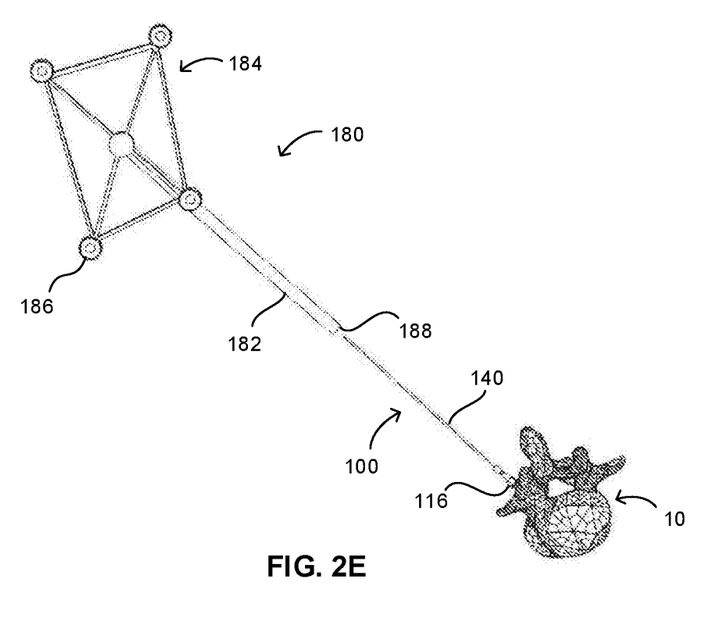

Another device that may be provided in a kit or system along with tap marker assembly 100 is a navigation tool 180, as best shown in FIG. 2E. Navigation tool 180 is configured to connect to tap marker 100' so that a pedicle can be easily registered and re-registered with a robotic navigation system. An exemplary robotic system and navigation system thereof that can be used in conjunction with navigation tool 180 and tap marker assembly 100' can be found disclosed in U.S. Publication No. 2018/0325608, which is hereby incorporated by reference herein in its entirety. In this regard, navigation tool 180 includes a cannulated shaft 182 and a navigation array 184. Cannulated shaft 182 has a tap engaging end 188 that is configured to engage tool engaging portion 116 of tap marker 100' so as to prevent relative rotation between the same. In addition, the cannulation of cannulated shaft 182 allows it to receive flexible member 140. Although, not shown, navigation tool 180 may also include a retaining ring similar to ring 160 so that when it is connected to tap marker 100', such ring engages groove 134 to prevent unintended axial movement of navigation tool 180 relative to tap marker 110.

Navigation array 184 includes a plurality of fiducials 186. Such fiducials 186 are configured to be recognized by a navigation system for registration of the pedicle to which navigation tool 180 is attached. In this regard, fiducials 186 can be adapted for active or passive navigation systems, such as for optical tracking. For example, where the navigation is a passive system, fiducials 186 may comprise a passive array of reflective fiducials that can reflect light, such as infrared light, emitted by the navigation system back to a detector of the navigation system or may comprise other visible markers, such as QR codes. Alternatively, where the navigation system is an active system, fiducials 186 may comprise an active array of fiducials, such as light emitting diodes (LED) that actively project light to a detector of the navigation system. Navigation array 184 could also include fiducials that are sensors configured to be read by the robotic system and translated into a position by the system for guidance of surgical instruments. Such sensors may include, for example, accelerometers, electromagnetic sensors, and the like. In addition, navigation array 184 can include a combination of the aforementioned fiducials. For example, array 184 can include both active and passive fiducials. As described further below, individual bones may move from their initial position during the surgical procedure. Navigation tool 180 can help register and re-register the location of the particular bone feature to which it is attached, such as a bone hole in a pedicle, so that the actual location of the bone feature can correspond to a preoperative image, such as a CT scan, within a virtual space.

The assemblies/devices described above can be used in open surgery, MIS, and surgeries performed manually, robotically or manually with robotic assistance (e.g., augmented reality, haptic guidance, and the like). For example, in a robotic or robotically assisted procedure, a pedicle is prepared by creating a pilot hole in a pedicle of a vertebra 10. This may be performed manually with a Jamshidi needle, drill, or the like, or performed robotically via a robotic drill or other hole generating instrument. Thereafter, tap marker assembly 100 is driven into the bone 10 through the pilot hole. This may be performed by sliding insertion/removal tool 170 over flexible member 140 and threadedly engaging inner threads 156 of insertion/removal body 150, as shown in FIG. 2A. The robotic or human operator may then use insertion/removal device 150 to drive threaded shaft 112 of tap 110 into bone 10 via torque delivered to tap head 114 via insertion/removal body 150, as shown in FIG. 2B. In doing so, tap 110 of tap marker 100' expands the pilot hole and cuts threads into the bone for subsequent insertion of a pedicle screw. After tap marker assembly 100 is fully inserted into the bone, insertion/removal device 150 may be pulled proximally and axially away from tap marker 100' so that retention ring 160 disengages tap marker post 130 and insertion/removal body 150 is removed from tap marker 100', as shown in FIG. 2C. With tap marker 100' inserted into bone 10, flexible member extends 140 out of the surgical site, as shown in FIG. 2D.

Figure 2F:
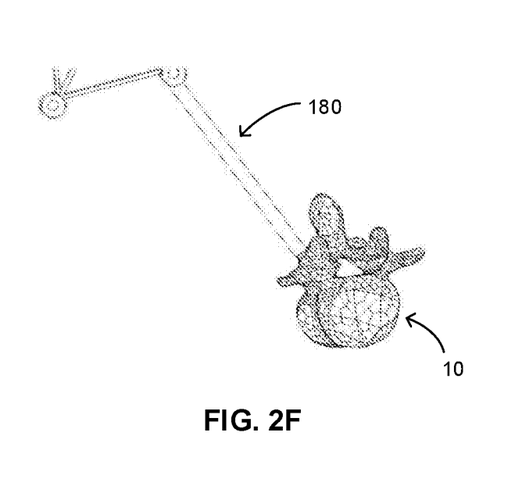

The location of the pedicle to which tap marker 100' is attached may be initially registered with a robotic system, such as the robotic system in aforementioned U.S. Publication No. 2018/0325608. In this regard, navigation tool 180 is connected to tap marker 100' by sliding cannulated shaft 182 over flexible member 140 until cannulated shaft 182 engages tool engagement portion 116 of tap 110, as best shown in FIGS. 2E and 2F. The robotic system may then proceed through a registration protocol in which the robot's navigation system detects the fiducials 186, actively or passively, and correlates the pose of fiducial array 184 to the patient's anatomy, e.g., pedicle and bone screw opening formed by tap 110. This initial registration may then allow the robot to proceed with inserting tap markers 100' into the remaining pedicles according to a preoperative plan. Alternatively, the human operator may insert tap markers 100' into each pedicle that is intended to receive a pedicle screw and allowing the robot to register each pedicle separately to obtain an accurate picture of the patient's anatomy and to correlate the same to a preoperative plan.

Figure 2G:
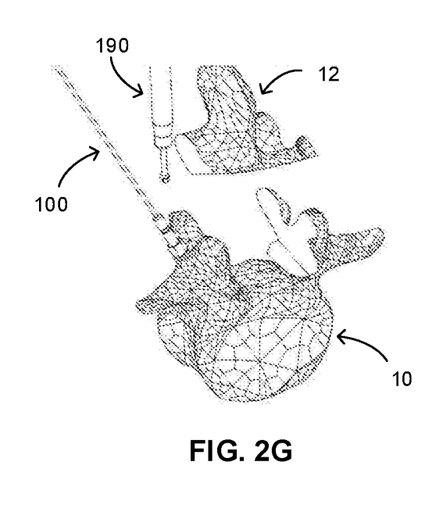

After registration, bony work can be performed. In order to ensure maximum operating space, flexible member 140 of each tap marker 100' can be moved/bent out of the way so as to not hinder such work. For example, a laminectomy may be performed on one or more vertebrae, as illustrated in FIG. 2G. In this regard, a cutting instrument 190, such as a rotating burr, is guided to the lamina 12 and is used to resect the lamina 12 from the vertebra 10. The lamina 12 may then be reattached with connectors (not shown) that expand the spinal canal. In other spinal procedures, such as in spinal fusion, other work may be performed such as a discectomy and implantation of an intervertebral implant (not shown) within the disc space. Other such work can include distraction and compression in which a distractor, such as the distractor disclosed in aforementioned U.S. Publication No, 2017/0196597, may be connected to tap marker posts 130 of adjacent vertebrae and then operated to distract and compress the vertebrae via tap markers 100'.

Once the bony work is performed, pedicle screws can be inserted into the bone 10. However, since the initial registration and due to the bony work that followed it, pedicles and tap markers 100' connected thereto may have shifted from their initially registered positions. In this regard, tap markers 100' may be used to re-register the bone to help ensure accurate engagement with the robot. Thus, once the bony work is performed, navigation tool 180 may be once again attached to each tap marker 100'. Robot may then proceed again through its registration protocol to register the locations of each pedicle and their respective bone holes. Once registration is completed, navigation tool 180 is removed and insertion/removal device 170 or some other removal device engages tool engaging feature 116 of tap marker 100' and operated to unthread each tap marker 100' from their respective pedicle. Alternatively, navigation tool 180 can be used to remove tap marker 100' from the bone. For example, navigation tool 180, as described above, may correspondingly engage with tool engagement portion 116 of tap 110 which allows a removal torque to be applied to tap 110 via navigation tool 180 for removal thereof. Additionally, navigation tool 180 can have a ratchet mechanism that allows the navigation tool 180 to rotate freely relative to tap 110 so that fiducial array 184 can be adjusted to face a navigation camera or the like of the robotic system.

Once tap marker 100' is removed, the same insertion/removal tool 170 may engage a pedicle screw and insert the same in each of the evacuated bone holes via the robotic system or manually under guidance by the robotic system. A stabilization rod may then be connected to pedicle screws of adjacent vertebrae for stabilization thereof.

In another method embodiment, tap marker 100' may be used in a manual MIS. In this regard, MIS incisions may be made over each pedicle that is to receive a pedicle screw. Each pedicle is prepared by creating a pilot hole such as via a Jamshidi needle, drill, or the like. Thereafter, a tap marker assembly 100 is connected to insertion/removal device 170 by engaging external threads 172 with internal threads 156 of body 150, as shown in FIG. 2A. Tap marker 100' is driven into a corresponding pedicle via insertion/removal device 170, as best shown in FIG. 2B, which transmits torque to insertion head 150 which transmits torque to tap 110 via tool engagement portion 116. Once tap marker assembly 100 is fully driven into the bone, insertion/removal device 170 and insertion head are removed by pulling insertion/removal device axially in a proximal direction, as shown in FIG. 2C. As this is done, retaining ring 162 disengages groove 134 in tap marker post 130 and insertion/removal body 150 is moved axially over flexible member 140 which is now exposed and extends from the MIS incision, as depicted in FIG. 2D. This is repeated for each pedicle that receives a pedicle screw.

Bony work may then be performed. This may be done via additional MIS incisions, such as over a disc space between adjacent vertebrae so that a discectomy can be performed and an intervertebral implant can be implanted within the prepared disc space, for example. As needed, flexible members 140 can be bent out of the way by the operator so as to have space to perform the work. Once completed, the operator may apply heat, such as via an inductor, to flexible members 140 to allow flexible members to return to their original configuration.

Thereafter, insertion/removal device 170 along with insertion/removal body 150 may re-engage each tap marker 100' and remove such tap marker 100' from the bone. Each tap marker 100' and associated pedicle is easily located and engaged due to flexible member 140 extending from the patient. A pedicle screw may then be inserted into the remaining bone hole which had been prepared via tap 110. Rods may then be connected to adjacent pedicle screws to help stabilize the vertebrae 10.

Tap markers 100' allow the operator to easily find the pedicles and bone hole location without the use of fluoroscopy or the like and thus can reduce the reliance on radiographic imagery in the operating theater so as to limit the exposure of the those present in the operating theater to radiation. Moreover the flexibility of flexible member 140 allows the operator to move flexible member 140 out of the way so that bony work may be performed unobstructed. This cannot be done with traditional k-wires as such k-wires are relatively rigid and attempting to bend such k-wires could result in the k-wires popping out of their respective bone holes. Moreover, bending a k-wire would result in a plastic deformation that would be difficult to return to its original orientation. However, flexible member 140, as mentioned above, may be made from a shape-memory or super elastic material that can return to its original orientation upon application of heat, for example.

Although the above described methods are particularly described in relation to spinal surgery, it should be understood that the inventive concepts described herein can be implemented in other orthopedic procedures. For example, tap marker 100' can be inserted into opposing bone fragments, such as those in a broken bone, prior to reduction of the same in order to track their relative movement throughout the procedure. This can help reduce the use of radiographic imagery during the procedure. In another example, tap marker 100' can be inserted into a femur and tibia in a total knee replacement. The distance between the markers can be robotically determined via visualization tool 180 to help assess flexion and extension gaps before the bones are resected and during the trialing phase to help confirm the height of the joint line and that collateral ligament laxity closely resembles that of the patient prior to the procedure. In each of these exemplary contexts, it should also be understood that the marker 100' is not required to be a tap for a subsequent bone screw although it certainly could be as described above. In that respect, the threaded element 112 of the marker 100' can have a smaller diameter than what would be used to tap for a subsequent bone screw. In addition, instead of a threaded element, like that of threaded shaft 112, a bone pin or the like could be used to secure the flexible member 140 and any sort of engagement feature like that of tool engagement portion 116. In such embodiment, the bone pin could have a groove at a proximal end thereof. A quick connect mechanism, such as one with a ball-bearing mechanism, can engage the groove on the pin to secure the flexible member and a tool engagement portion thereto. Alternatively, a drill-bit or other cutting tool could be used in lieu of the threaded element 112 such that flexible member 140 and tool engagement portion 116 extend from the drill-bit which is left in the bone after drilling a hole therein.

Moreover, it should also be understood that while tap marker 100' is described as tapping a hole for a subsequent bone screw, particularly a pedicle screw, it is not required that a subsequent pedicle screw be inserted into the opening. For example, tap marker 100' may be used for distraction and compression and/or visualization, for example, in a spinal fusion procedure where no pedicle screws and connecting rods are implanted. In addition, while tap marker assembly 100 is described as including an insertion/removal body 150, it should be understood that such body 150 is optional as it can help reduce the total number of instruments used in the operating theater, as described above. However, tap marker 100' may have a dedicated insertion/removal tool that is configured to insert and/or remove tap marker 100' from the bone without the aid of body 150. Such dedicated tool may have a feature adapted to engage tool engagement portion 116 of tap marker 100' to insert and/or remove tap marker 100'.

Figure 3A:
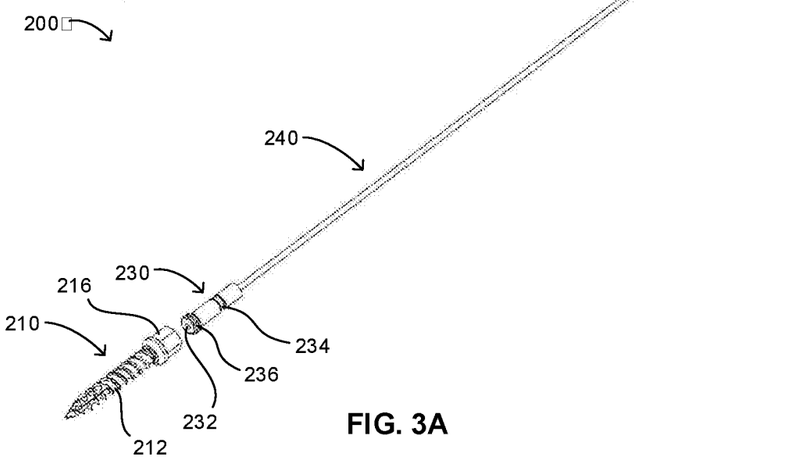
FIG. 3A is a partially exploded view of a tap marker according to an additional embodiment of the present disclosure.
Figure 3B:
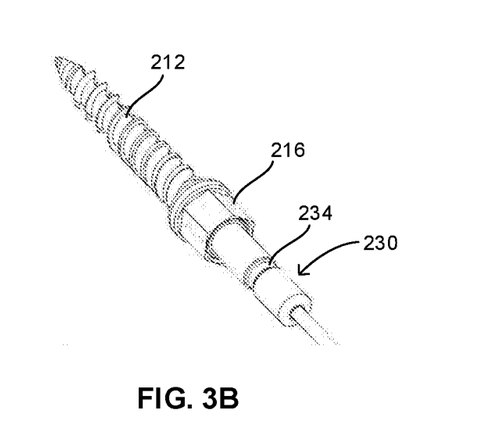
FIG. 3B is an enhanced view of a portion of the tap marker of FIG. 3A.
Figure 3C:
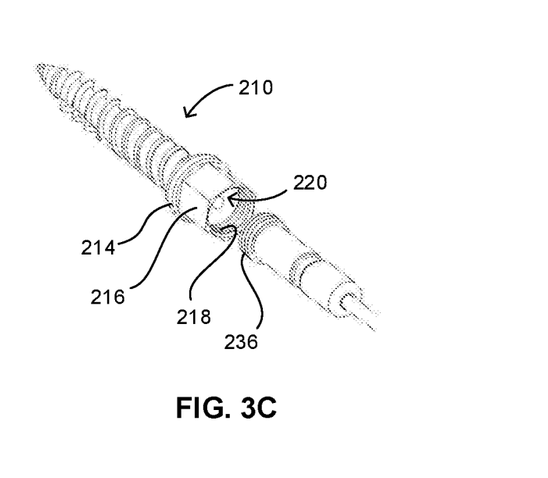
FIG. 3C is an enhanced partially exploded view of the tap marker of FIG. 3B.

FIGS. 3A-3C depict a tap marker 200' according to another embodiment of the present disclosure. Tap marker 200' is similar to tap marker 100' in that it includes a tap 210, crimp ring 222, tap marker post 230, and a flexible member 240 extending therefrom. In addition, insertion/removal body 150 may connect thereto as described above. However, unlike tap marker 100', post 230 is connected to tap 210 via a threaded connection between inner threads 218 of tap 210 and external threads 236 of post 230. Thus, tap head 214 includes a female thread 218 within its proximal opening while post 230 includes male thread 236 at a distal end of post 230. This allows tap marker 100' to be completely disassembled after each procedure for sterilization.

Figure 4A:
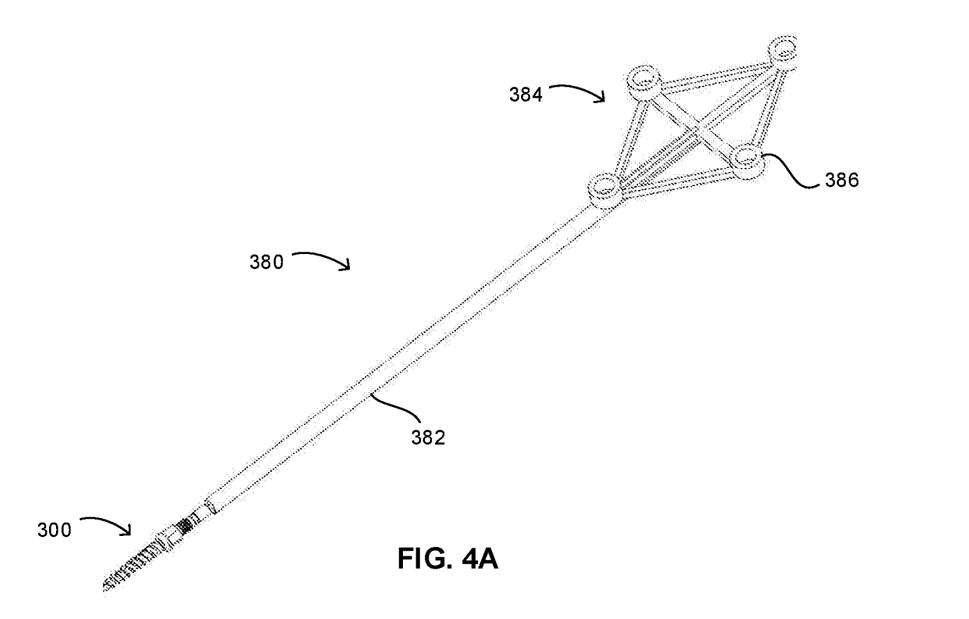
FIG. 4A is a perspective view of a navigation tool and tap marker assembly according to a further embodiment of the present disclosure.
Figure 4B:
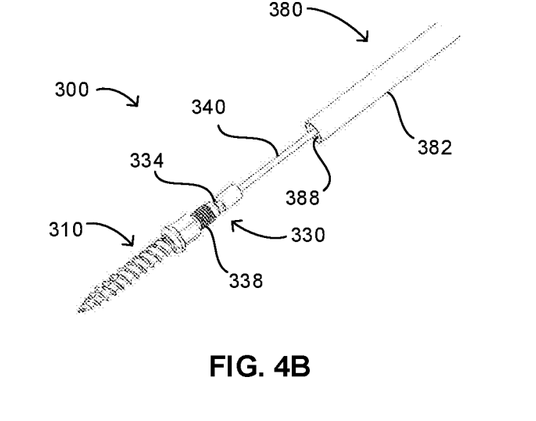
FIGS. 4B and 4C are enhanced views of portions of the navigation tool and tap marker assembly of FIG. 4A in respective first and second configurations.
Figure 4C:
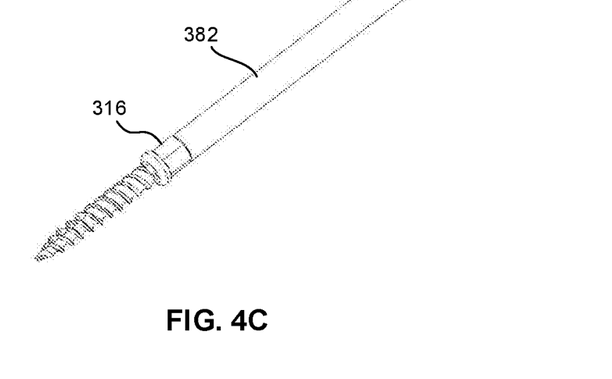

FIGS. 4A-4C depict a tap marker 300' and navigation tool 380 each according to additional embodiments of the present disclosure. Tap marker 300' is similar to tap markers 100' and 200' and thus include a tap 310, crimp ring (not shown), tap marker post 330, and flexible member 340. However, tap marker post 330 includes external threads 337 helically extending about a portion thereof that extends from tap 310. Navigation tool 380 similarly includes female threads 388 within its cannulated shaft 382. Thus, when navigation tool 380 is connected to tap marker 300', instead of engaging tool engaging portion 316 like that of tap marker 100' and tool 180, navigation tool 380 threadedly engages external threads 338 of tap marker post 330. Such configuration may be advantageous in that such threaded connection may limit toggle between tap marker 300' and navigation tool 380 as such toggle can result in inaccuracies in registration with a navigation system.

In an even further embodiment similar to that of tap marker 300', instead of the external threads 338 being positioned on an exterior of post 330, the threads 338 may be positioned on tool engagement portion 316 for connection to shaft 382 and/or other instruments and adapters, such as insertion body 150. In such an embodiment, post 330 may not be included. Indeed, posts 130, 230, and 330 are optionally included in their respective tap markers. A cap, or the like, can retain the crimp ring in tap marker head in its stead. Also, as an alternative to the external threads 338, a flange may be provided on tool engagement portion 316 in lieu of the intersecting planar surfaces so as to engage a quick-connect mechanism of a corresponding instrument/tool, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal marking system comprising:
    a marker having a threaded member and a flexible member connected to the threaded member, the flexible member having a length longer than that of the threaded member; and
    a navigation tool having a shaft configured to connect to the threaded member, the navigation tool also having a navigation array connected to the shaft, the navigation array having a plurality of fiducials that are configured to communicate with a robotic system,
    wherein the threaded member has a threaded shaft with at least one flute and a head extending from the threaded shaft, the flexible member being connected to and extending from the head, and
    wherein the marker further includes a post received within an opening in the head and extending therefrom, the post having an opening extending entirely therethrough, the flexible member extending through the opening of the post.

2. The system of claim 1, wherein the plurality of fiducials actively emit light or passively reflect light.

3. The system of claim 1, wherein the marker further includes a crimp ring crimped about an end of the flexible member and disposed within the opening in the head of the threaded member.

4. The system of claim 3, wherein the head of the threaded member includes a tool engagement portion comprised of a plurality of intersecting planar faces.

5. The system of claim 4, wherein the shaft of the navigation tool has a plurality of intersecting planar faces configured to interface with those of the tool engagement portion to prevent relative rotation between the navigation tool and the marker when the navigation tool is connected to the threaded member.

6. The system of claim 1, further comprising an insertion body removably connectable to the marker, the insertion body having a head and a shaft extending from the head, the head having a threaded inner surface.

7. The system of claim 6, wherein the threaded member has a male engagement portion and the shaft of the insertion body has a female engagement portion configured to receive the male engagement portion of the threaded member.

8. The system of claim 7, wherein the male and female engagement portions each have corresponding intersecting planar faces and when said planar faces of the threaded member and the insertion body interface, relative rotation between the threaded member and the insertion body is prevented.

9. The system of claim 8, further comprising a retaining ring configured to engage the post and the insertion body to limit relative axial movement between the post and the insertion body.

10. The system of claim 7, wherein the insertion body defines an opening extending therethrough such that when the male and female engagement portions engage, the flexible member extends from one end of the insertion body and the threaded member extends from another end of the insertion body.

11. The system of claim 6, further comprising a driver having a threaded exterior surface configured to threadedly engage the threaded inner surface of the insertion body.

12. A tap marker assembly, comprising:
    a tap marker comprising a tap having a threaded shaft and a head extending from the threaded shaft, the tap marker also having a flexible member connected to and extending from the head of the tap, the flexible member having a length greater than that of the tap; and
    an insertion body removably connected to the tap and having an opening extending through the insertion body such that the flexible member extends from one end of the insertion body and the tap extends from another end of the insertion body when the insertion body is connected to the tap,
    wherein the tap marker further includes a post connected to the head of the tap and extending therefrom, the post having a longitudinal opening through which the flexible member extends and a circumferential groove extending about an axis defined by the longitudinal opening, and
    wherein the insertion body is connected to the post via a retention ring positioned between the insertion body and the post and at least partially within the circumferential groove.

13. The assembly of claim 12, wherein the tap includes a male engagement portion and the opening of the insertion body includes a female engagement portion configured to mate with the male engagement portion of the tap.

14. The assembly of claim 13, wherein the male and female engagement portions each include corresponding planar faces that interface with each other to prevent relative rotation between the tap and the insertion body.

15. The assembly of claim 13, wherein the male and female engagement portions each comprise corresponding threaded surfaces for threaded connection of the same.

16. The assembly of claim 12, wherein the insertion body includes a head and a shaft extending from the head, the head of the insertion body having a larger cross-sectional dimension than the shaft of the insertion body and having a threaded inner surface for engagement with threads of a driver.

* * * * *